(12) United States Patent
Akino

(10) Patent No.: US 8,705,688 B2
(45) Date of Patent: Apr. 22, 2014

(54) MEDICAL IMAGE PROCESSING APPARATUS, X-RAY COMPUTED TOMOGRAPHY APPARATUS, AND MEDICAL IMAGE PROCESSING METHOD

(75) Inventor: Naruomi Akino, Nashishiobara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 0 days.

(21) Appl. No.: 13/329,754

(22) Filed: Dec. 19, 2011

(65) Prior Publication Data

US 2012/0093279 A1    Apr. 19, 2012

Related U.S. Application Data

(63) Continuation of application No. PCT/JP2011/071014, filed on Sep. 14, 2011.

(30) Foreign Application Priority Data

Oct. 13, 2010   (JP) ................................. 2010-230340

(51) Int. Cl.
*A61B 6/03* (2006.01)

(52) U.S. Cl.
USPC .............................................................. 378/5

(58) Field of Classification Search
USPC ............................... 378/5, 98.9; 382/130, 131
See application file for complete search history.

(56) References Cited

U.S. PATENT DOCUMENTS

| | | | | |
|---|---|---|---|---|
| 3,848,130 A | * | 11/1974 | Macovski | ..................... 378/98.9 |
| 3,965,358 A | * | 6/1976 | Macovski | ......................... 378/5 |
| 4,029,963 A | * | 6/1977 | Alvarez et al. | ..................... 378/5 |
| 4,686,695 A | * | 8/1987 | Macovski | ...................... 378/146 |
| 4,788,706 A | * | 11/1988 | Jacobson | ....................... 378/207 |
| 5,481,584 A | * | 1/1996 | Tang et al. | .................... 378/98.9 |
| 5,490,218 A | * | 2/1996 | Krug et al. | ..................... 382/100 |
| 5,524,133 A | * | 6/1996 | Neale et al. | ....................... 378/53 |

(Continued)

FOREIGN PATENT DOCUMENTS

| | | |
|---|---|---|
| CN | 101249000 A | 8/2008 |
| CN | 101632591 A | 1/2010 |

(Continued)

OTHER PUBLICATIONS

International Search Report corresponding to International Application No. PCT/JP2011/071014 mailed on Oct. 25, 2011.

(Continued)

*Primary Examiner* — Irakli Kiknadze
(74) *Attorney, Agent, or Firm* — Yoshida & Associates, LLC

(57) ABSTRACT

According to one embodiment, a medical image processing apparatus includes an image storage unit, an estimation unit, a combination ratio determination unit, and a combined image generation unit. The estimation unit is configured to estimate an abundance ratio of one of a first and second substances to the other for each pixel based on attenuation coefficients of the first substance which correspond to a first and second energies, the attenuation coefficients of a second substance which correspond to the first and second energies, and pixel values of a first and second medical images. The combination ratio determination unit is configured to determine combination ratios of pixel values between the first and second medical images for each pixel based on the abundance ratios of the first and second substances and the attenuation coefficients of the first and second substances which are associated with a target energy.

2 Claims, 10 Drawing Sheets

(56) References Cited

U.S. PATENT DOCUMENTS

| | | | |
|---|---|---|---|
| 6,173,034 B1* | 1/2001 | Chao | 378/37 |
| 6,597,759 B2* | 7/2003 | Mazess et al. | 378/53 |
| 6,950,494 B2* | 9/2005 | Vija et al. | 378/62 |
| 6,987,833 B2* | 1/2006 | Du et al. | 378/98.9 |
| 6,999,549 B2* | 2/2006 | Sabol et al. | 378/5 |
| 7,023,957 B2* | 4/2006 | Bijjani et al. | 378/57 |
| 7,050,530 B2* | 5/2006 | Heismann | 378/5 |
| 7,885,373 B2* | 2/2011 | Liu et al. | 378/5 |
| 2003/0215120 A1* | 11/2003 | Uppaluri et al. | 382/128 |
| 2004/0184574 A1* | 9/2004 | Wu et al. | 378/5 |
| 2004/0223585 A1* | 11/2004 | Heismann et al. | 378/54 |
| 2005/0100125 A1* | 5/2005 | Heismann | 378/5 |
| 2007/0217570 A1* | 9/2007 | Grasruck et al. | 378/53 |
| 2008/0260092 A1* | 10/2008 | Imai et al. | 378/5 |
| 2009/0207967 A1* | 8/2009 | Liu et al. | 378/5 |
| 2009/0262997 A1 | 10/2009 | Zou | |
| 2009/0304249 A1* | 12/2009 | Wu | 382/131 |
| 2010/0014737 A1* | 1/2010 | Ruhrnschopf et al. | 382/131 |

FOREIGN PATENT DOCUMENTS

| | | |
|---|---|---|
| JP | 2005-245657 A | 9/2005 |
| JP | 2006-320464 A | 11/2006 |
| JP | 2009-153829 A | 7/2009 |
| JP | 2009-261942 A | 11/2009 |

OTHER PUBLICATIONS

The International Search Report corresponding to International Application No. PCT/JP2011/071014 mailed on Oct. 25, 2011.
Chinese Office Action with its English translation for Chinese Patent Application No. 201180002262.6 mailed on Jan. 10, 2014.

* cited by examiner

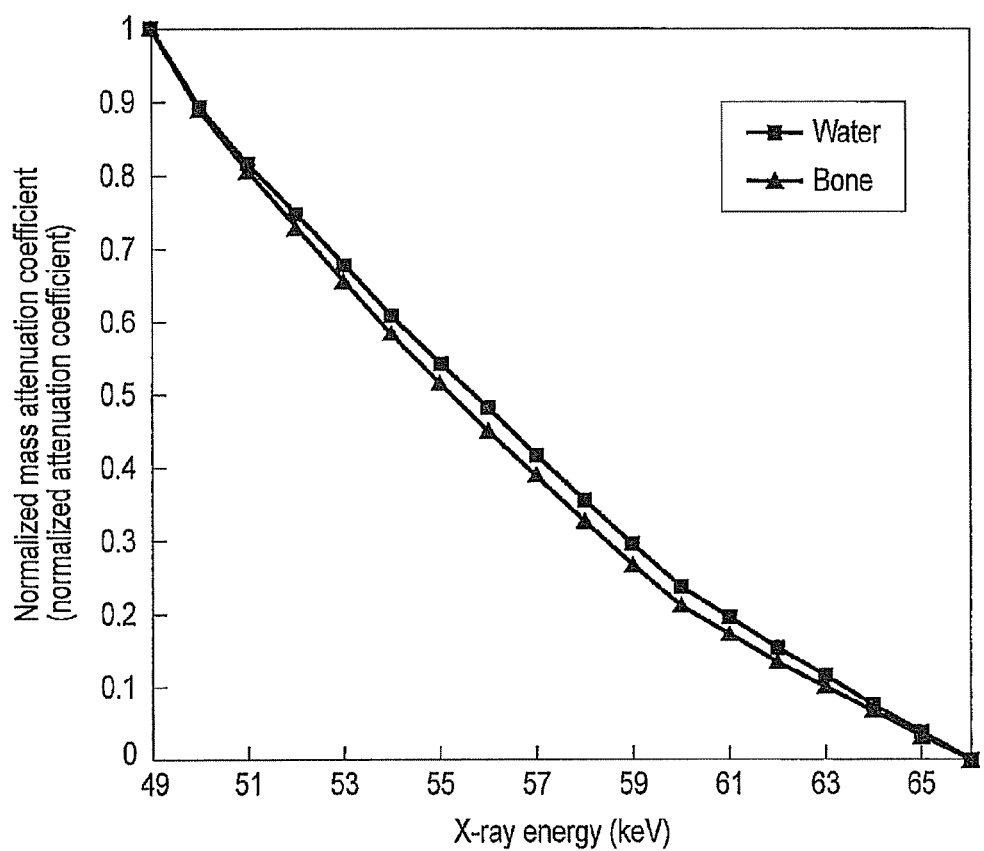
F I G. 2

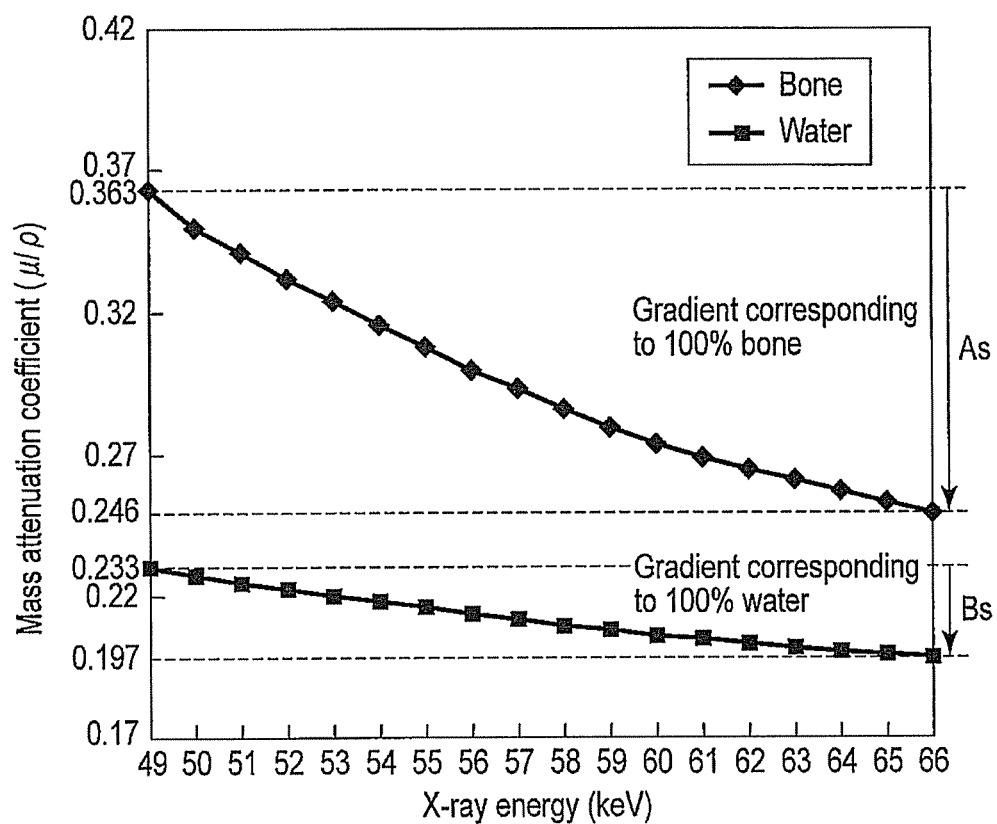
F I G. 3

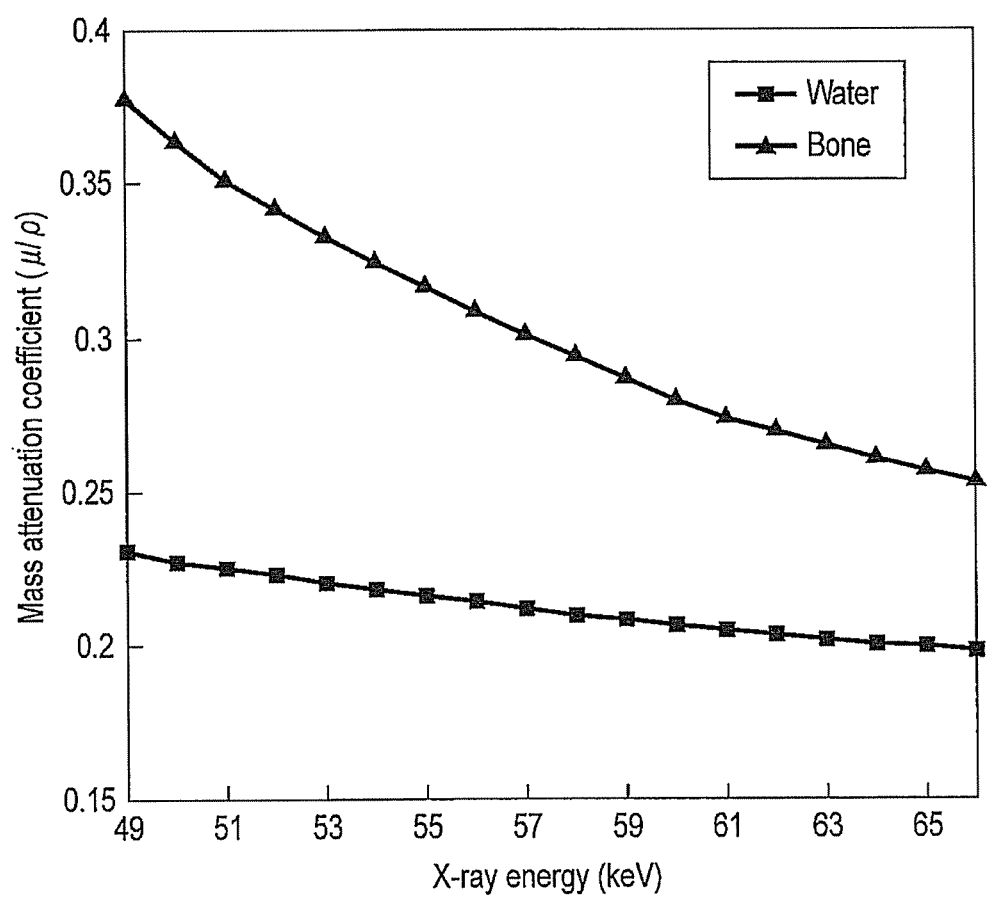
F I G. 4

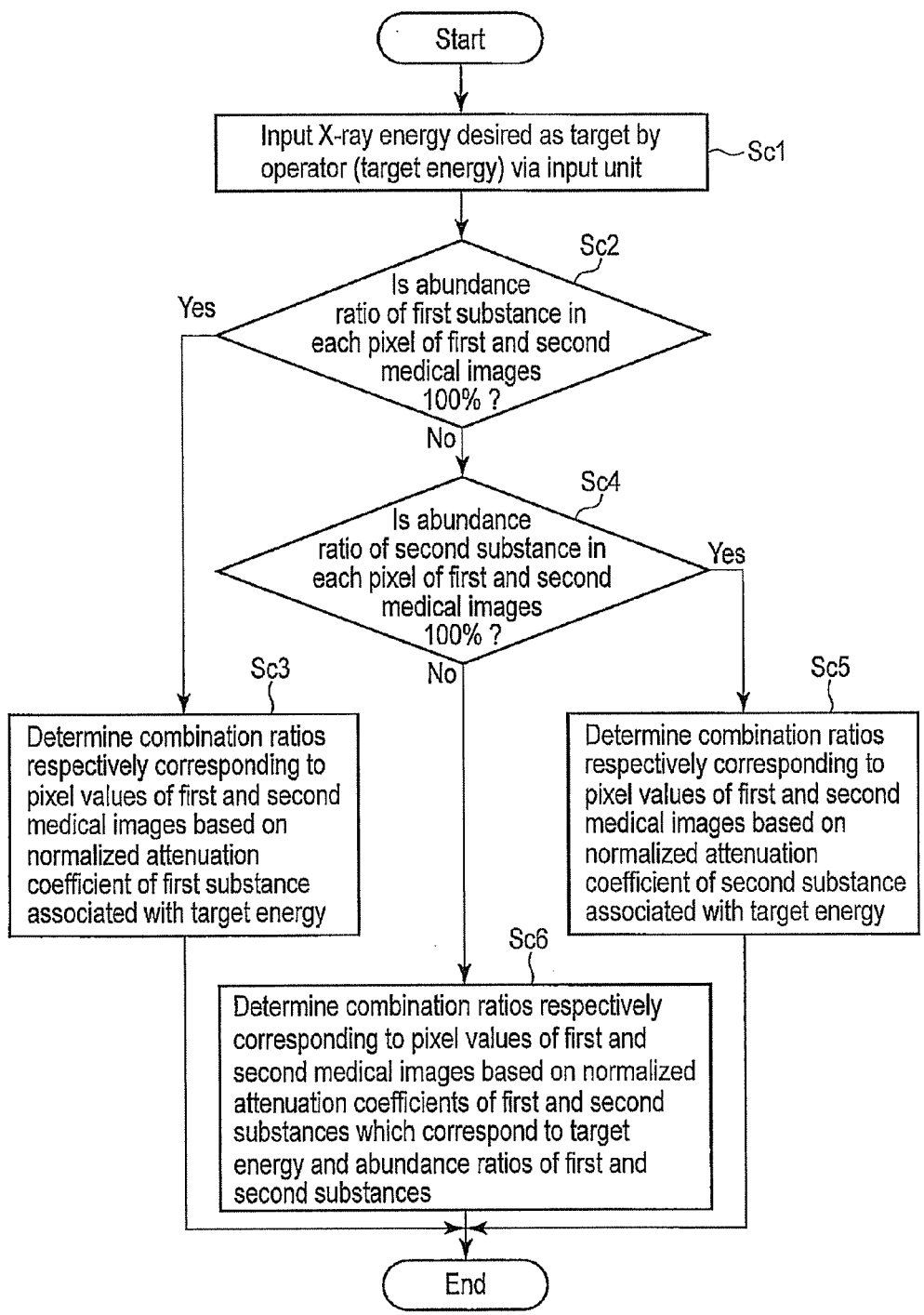
F I G. 9

MEDICAL IMAGE PROCESSING APPARATUS, X-RAY COMPUTED TOMOGRAPHY APPARATUS, AND MEDICAL IMAGE PROCESSING METHOD

CROSS REFERENCE TO RELATED APPLICATIONS

This application is a Continuation Application of PCT Application No. PCT/JP2011/071014, filed Sep. 14, 2011 and based upon and claiming the benefit of priority from prior Japanese Patent Application No. 2010-230340, filed Oct. 13, 2010, the entire contents of all of which are incorporated herein by reference.

FIELD

Embodiments described herein relate generally to a medical image processing apparatus, an X-ray computed tomography apparatus, and a medical image processing method.

BACKGROUND

There has conventionally been available a technique of obtaining an image with reduced image noise by averaging medical images respectively corresponding to two different kinds of X-ray energies. There is also available an X-ray computed tomography apparatus in which an X-ray generation unit generates X-rays having two different kinds of energy spectra. There is available a technique of reconstructing a medical image corresponding to the X-ray energy desired by the operator (to be referred to as a target energy hereinafter) by using the projection data of an object which respectively correspond to two kinds of energy spectra.

Some medical images generated by averaging, however, do not correspond to target energies. Furthermore, it requires much time to reconstruct a medical image corresponding to a target energy by using the projection data of an object which respectively correspond to two kinds of energy spectra.

BRIEF DESCRIPTION OF THE DRAWINGS

FIG. 2 is a graph showing the normalized attenuation coefficient dependence of each of the first and second substances on changes in X-ray energy according to the first embodiment.

FIG. 3 is a graph showing the first and second attenuation coefficient ratios, together with the mass attenuation coefficient dependence of each of the first and second substances on X-ray energy, according to the first embodiment.

FIG. 4 is a graph showing the mass attenuation coefficient dependence of each of the first and second substances on X-ray energy according to the first embodiment.

FIG. 9 is a flowchart showing a procedure for processing in step Sa3 in FIG. 7 according to the first embodiment.

DETAILED DESCRIPTION

Figure 1:
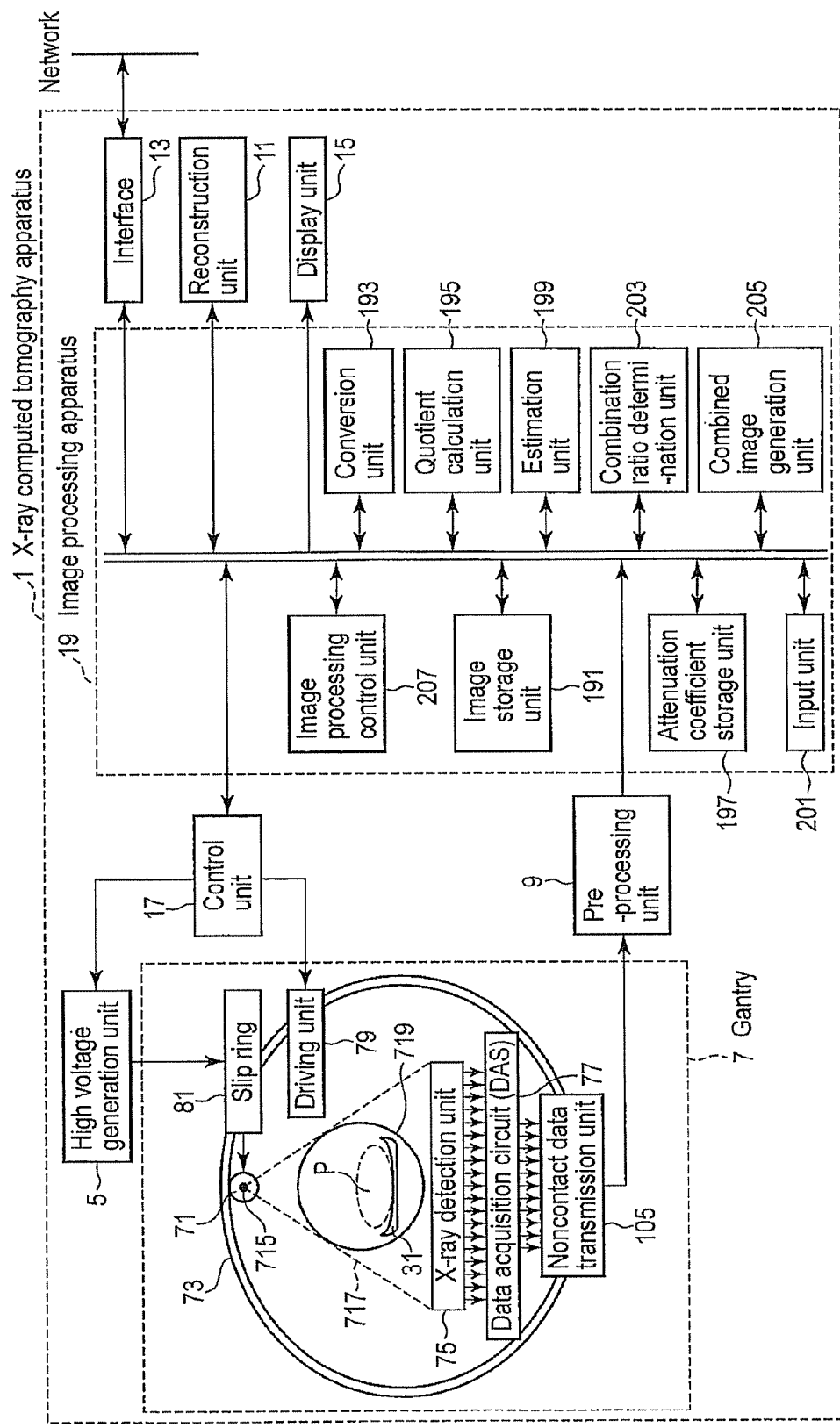
FIG. 1 is a view showing the arrangement of an X-ray computed tomography apparatus according to the first embodiment.

In general, a medical image processing apparatus according to an embodiment includes an image storage unit, an estimation unit, a combination ratio determination unit, and a combined image generation unit.

The image storage unit is configured to store a first medical image and a second medical image respectively originating from X-rays of a first energy and a second energy.

The estimation unit is configured to estimate an abundance ratio of one of a first substance and a second substance to the other for each pixel based on attenuation coefficients of the first substance which correspond to the first energy and the second energy, attenuation coefficients of the second substance which correspond to the first energy and the second energy, and pixel values of the first medical image and the second medical image.

The combination ratio determination unit is configured to determine combination ratios of pixel values between the first medical image and the second medical image for each pixel based on the abundance ratios of the first substance and the second substance and the attenuation coefficients of the first substance and the second substance which are associated with a target energy.

The combined image generation unit is configured to generate a combined image associated with the target energy from the first medical image and the second medical image by using the determined combination ratios.

An X-ray computed tomography apparatus 1 according to an embodiment will be described below with reference to the accompanying drawings. Note that the X-ray computed tomography apparatus 1 includes various types of apparatuses, e.g., a rotate/rotate-type apparatus in which an X-ray generation unit 71 and an X-ray detection unit 75 rotate together around an object, and a stationary/rotate-type apparatus in which an array of many X-ray detection elements is fixed in the form of a ring, and only the X-ray generation unit 71 rotates around an object. This embodiment can be applied to either type. In order to reconstruct image data, projection data corresponding to one rotation around an object, i.e., 360°, is required, or (180° + fan angle) projection data is required in the half scan method.

The embodiment can be applied to either of these reconstruction schemes. As mechanisms of changing incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor such as selenium by X-rays and migration of the electron-hole pairs to an electrode, i.e., a photoconductive phenomenon. As an X-ray detection element, either of these schemes can be used. Recently, with advances toward the commercialization of a so-called multi-tube type X-ray computed tomography apparatus having a plurality of pairs of X-ray generation units 71 and X-ray detection units 75 mounted on a rotating ring 73, related techniques have been developed. The embodiment can be applied to both a conventional single-tube type X-ray computed tomography apparatus and a multi-tube type X-ray computed tomography apparatus. The single-tube type X-ray computed tomography apparatus will be exemplified here.

Note that the same reference numerals in the following description denote constituent elements having almost the same functions and arrangements, and a repetitive description will be made only when required.

(First Embodiment)

FIG. 1 is a view showing the arrangement of the X-ray computed tomography apparatus 1 according to the first embodiment. The X-ray computed tomography apparatus 1 according to the first embodiment includes a high voltage generation unit 5, a gantry 7, a preprocessing unit 9, a reconstruction unit 11, an interface 13, a display unit 15, a control unit 17, and an image processing apparatus 19.

The high voltage generation unit 5 generates high voltages to be applied to the X-ray generation unit 71. The high voltage generation unit 5 generates a plurality of high voltages under the control of the control unit 17.

The gantry 7 accommodates a rotation support mechanism. The rotation support mechanism includes the rotating ring 73 and a driving unit 79 (electric motor) which drives the rotation of the ring and a ring support mechanism which supports the rotating ring 73 so as to allow it to rotate about a rotation axis Z.

The X-ray generation unit 71 and an area detector (to be referred to as the X-ray detection unit 75 hereinafter) which is also called a two-dimensional array type or multi-array type detector are mounted on the rotating ring 73.

Upon reception of voltages and currents from the high voltage generation unit 5 via a slip ring 81, the X-ray generation unit 71 emits X-rays from a focus 715 of X-rays. When the high voltage generation unit 5 applies different voltages (to be referred to as tube voltages hereinafter), the X-ray generation unit 71 generates X-rays having a plurality of energy spectra respectively corresponding to a plurality of tube voltages. For the sake of a simple description, assume that there are two kinds of tube voltages, namely 66 kV and 135 kV. Note that there may be a plurality of tube voltages. In addition, the average energy of X-ray energy spectra will be referred to as an X-ray energy. For example, the X-ray energies corresponding to tube voltages 80 kV and 135 kV are 49 keV and 66 keV, respectively. The X-ray energies, 49 keV and 66 keV, will be referred to as the first and second energies, respectively. If there are plurality of kinds of tube voltages, a plurality of X-ray energies respectively correspond to the plurality of tube voltages. Note that the first energy may be an X-ray energy different from 49 keV. The second energy is not limited to an energy of 66 keV as long as it is higher than the first energy.

A collimator unit attached to the X-ray emission window of the X-ray generation unit 71 shapes X-rays emerging from the focus 715 of X-rays into, for example, a cone beam shape (pyramidal shape). A dotted line 717 indicates the irradiation range of X-rays. The X-axis is a straight line which is perpendicular to the rotation axis Z and passes through the focus 715 of emitted X-rays. The Y-axis is a straight line perpendicular to the X-axis and the rotation axis Z. For the sake of convenience, this XYZ coordinate system is a rotational coordinate system which rotates about the rotation axis Z.

The X-ray detection unit 75 is attached at the position and angle at which it faces the X-ray generation unit 71 through the rotation axis Z. The X-ray detection unit 75 includes a plurality of X-ray detection elements. The following description will be made on the assumption that a single X-ray detection element forms a single channel. A plurality of channels are perpendicular to the rotation axis Z and are two-dimensionally arrayed in two directions, namely the Z direction and an arc direction (channel direction) with the radius coinciding with the distance from the focus 715 of emitted X-rays as the center to the center of the light-receiving portion of an X-ray detection element corresponding to one channel. The X-ray detection unit 75 may also be constituted by a plurality of modules each formed by one array of a plurality of X-ray detection elements. Each module is one-dimensionally arrayed in almost the arc direction along the channel direction.

In addition, a plurality of X-ray detection elements may be two-dimensionally arrayed in two directions, namely the channel direction and the slice direction. That is, a two-dimensional array is formed by arraying a plurality of channels, each arrayed one-dimensionally along the channel direction, in the slice direction. The X-ray detection unit 75 having such a two-dimensional array of X-ray detection elements may be formed by arraying, in the slice direction, the plurality of modules, each arrayed one-dimensionally in the almost arc direction.

When starting imaging or scanning, the operator inserts a top 31 on which an object P is placed into a cylindrical imaging area 719 between the X-ray generation unit 71 and the X-ray detection unit 75. A data acquisition circuit 77 called DAS (Data Acquisition System) is connected to the output of the X-ray detection unit 75.

An I-V converter, integrator, amplifier, and analog/digital converter are attached to the data acquisition circuit 77 for each channel. The I-V converter converts a current signal on each channel of the X-ray detection unit 75 into a voltage. The integrator periodically integrates such voltage signals in synchronism with an X-ray exposure period. The amplifier amplifies an output signal from the integrator. The analog/digital converter converts an output signal from the amplifier into a digital signal. A preprocessing unit 9 receives the data (pure raw data) output from the data acquisition circuit 77 via a noncontact data transmission unit 105 using magnetic transmission/reception or optical transmission/reception.

The preprocessing unit 9 executes preprocessing for the pure raw data output from the data acquisition circuit 77. The preprocessing includes, for example, sensitivity nonuniformity correction processing between channels and the processing of correcting an extreme decrease in signal intensity or signal omission due to an X-ray absorber, mainly a metal portion. The data (called raw data or projection data; projection data in this case) output from the preprocessor 9 immediately before reconstruction processing is stored in a projection data storage unit including a magnetic disk, magneto-optical disk, or semiconductor memory in association with data representing view angles at the time of data acquisition.

Note that projection data is a set of data values corresponding to the intensities of X-rays transmitted through the object. For the sake of descriptive convenience, a set of projection data acquired almost simultaneously by one shot at the same view angle throughout all channels is called a projection data set. View angles are represented by angles in the range of 0° to 360° which represent the respective positions on a circular orbit centered on the rotation axis Z along which the X-ray generation unit 71 revolves, with the position of the uppermost position on the orbit being 0°. Projection data corresponding to each channel of a projection data set is identified by a view angle, cone angle, and channel number. Alternatively, projection data corresponding to each channel of a projection data set may be identified in accordance with the energy of X-rays emitted from the X-ray generation unit 71.

The reconstruction unit 11 has a function of reconstructing an almost cylindrical three-dimensional image by a Feldkamp (Feldkamp-Davis-Kress) method or cone beam reconstruction method based on a projection data set in the view angle range of 360° or 180°+fan angle. The reconstruction unit 11 has a function of reconstructing a two-dimensional image (tomogram) by, for example, a fan beam reconstruction method (also called a fan beam/convolution/back projection method) or a filtered backprojection method. The Feldkamp method is a reconstruction method to be used when a projection ray crosses a reconstruction plane like a cone beam. The Feldkamp method is an approximate image reconstruction method in which a cone beam is regarded as a fan projection beam in convolution, and a reverse projection is processed along a ray in scanning on the premise that the cone angle is small. A cone beam reconstruction method is a reconstruction method as a method which suppresses cone angle errors more than the Feldkamp method, in which projection data is corrected in accordance with the angle of a ray with respect to a reconstruction plane.

The reconstruction unit 11 reconstructs a plurality of medical images originating from a plurality of X-ray energies. More specifically, the reconstruction unit 11 generates the first medical image corresponding to the first energy. The reconstruction unit 11 generates the second medical image corresponding to the second energy. A plurality of medical images respectively corresponding to a plurality of X-ray energies are stored in an image storage unit 191 of the image processing apparatus 19 (to be described later). Note that the plurality of medical images corresponding to the X-ray energies may be stored in an external storage device (not shown) via the interface 13 (to be described later).

The interface 13 connects the X-ray computed tomography apparatus 1 or the image processing apparatus 19 to an electronic communication circuit (to be referred to as a network hereinafter). A radiology information management system (not shown), a hospital information system (not shown), and the like are connected to the network.

The display unit 15 displays the medical image reconstructed by the reconstruction unit 11, the medical image processed by the image processing apparatus 19 (to be described later), conditions set for X-ray computed tomography, and the like.

The control unit 17 functions as the main unit of the X-ray computed tomography apparatus 1. The control unit 17 includes a CPU (Central Processing Unit) and memory (neither of which is shown). The control unit 17 controls the high voltage generation unit 5, the gantry 7, and the like for X-ray computed tomography based on the examination schedule data and control programs stored in a memory (not shown). More specifically, the control unit 17 temporarily stores, in a memory (not shown), information such as operator's instructions, image processing conditions, imaging conditions (settings of a plurality of tube voltages and a plurality of X-ray energies) sent from an input unit 201 (to be described later) and a radiology information management system (not shown), a hospital information system (not shown), and the like. The control unit 17 controls the high voltage generation unit 5 and the gantry 7 based on these pieces of information temporarily stored in the memory. The control unit 17 reads out control programs for executing predetermined image generation and display processes and the like from a storage unit (not shown), expands the programs in its own memory, and executes computation, processing, and the like associated with various kinds of processes.

The image processing apparatus 19 includes an image storage unit 191, a conversion unit 193, a quotient calculation unit 195, an attenuation coefficient storage unit 197, an estimation unit 199, the input unit 201, a combination ratio determination unit 203, a combined image generation unit 205, and an image processing control unit 207.

The image storage unit 191 stores the medical image reconstructed by the reconstruction unit 11 in correspondence with a tube voltage or X-ray energy. More specifically, the image storage unit 191 stores the first and second medical images respectively corresponding to the first and second energies. The first and second medical images are medical images which differ only in tube voltage, i.e., X-ray energy.

The conversion unit 193 converts a pixel value of a medical image stored in the image storage unit 191 into a mass attenuation coefficient for each pixel. More specifically, the conversion unit 193 converts the CT value (Hounsfield unit) of each of a plurality of pixels of each of the first and second medical images into a mass attenuation coefficient. With this conversion, the conversion unit 193 generates the first attenuation map in which a pixel value of the first medical image is converted into a mass attenuation coefficient for each pixel. The conversion unit 193 generates the second attenuation map in which a pixel value of the second medical image is converted into a mass attenuation coefficient for each pixel. If a plurality of medical images respectively corresponding to a plurality of X-ray energies are stored in the image storage unit 191, the conversion unit 193 generates the first and second attenuation maps for the plurality of medical images respectively corresponding to the first and second energies selected by the operator via the input unit 201 (to be described later).

The quotient calculation unit 195 generates a division map based on the first and second attenuation maps. More specifically, the quotient calculation unit 195 calculates a quotient by dividing a mass attenuation coefficient in the first attenuation map by a mass attenuation coefficient in the second attenuation map for each pixel. The quotient is the ratio of a mass attenuation coefficient of the first energy to a mass attenuation coefficient of the second energy.

The attenuation coefficient storage unit 197 stores the normalized mass attenuation coefficient (to be referred to as the normalized attenuation coefficient hereinafter) dependence of each of the first and second substances on X-ray energy. FIG. 2 is a graph showing the normalized attenuation coefficient dependence of each of the first and second substances on X-ray energy. The abscissa of FIG. 2 represents the X-ray energies in keV. The ordinate of FIG. 2 represents the normalized attenuation coefficient of each of the first and second substances. More specifically, a normalized attenuation coefficient is the value obtained by normalizing a mass attenuation coefficient of each of the first and second substances based on the mass attenuation coefficients of the first and second energies. The triangle marks in FIG. 2 represent the normalized attenuation coefficient change dependence of the first substance (e.g., the bone or contrast medium) on changes in X-ray energy in increments of 0.5 keV. The square marks in FIG. 2 represent the normalized attenuation coefficient change dependence of the second substance (e.g., water) on changes in X-ray energy in increments of 0.5 keV. Note that the attenuation coefficient storage unit 197 may store a correspondence table between target energies input by the operator via the input unit 201 (to be described later) and the normalized attenuation coefficients of the first and second substances.

The attenuation coefficient storage unit 197 stores the ratio of the mass attenuation coefficient of the first energy (to be referred to as the first attenuation coefficient ratio hereinafter) to the mass attenuation coefficient of the second energy with respect to the first substance. The attenuation coefficient storage unit 197 stores the ratio of the mass attenuation coefficient of the first energy (to be referred to as the second attenuation coefficient ratio hereinafter) to the mass attenuation coefficient of the second energy with respect to the second substance. FIG. 3 is a graph showing the first and second attenuation coefficient ratios, together with the mass attenuation coefficient dependence of each of the first and second substances on X-ray energy. The rhombic marks in FIG. 3 represent the mass attenuation coefficients of the first substance (e.g., the bone or contrast medium) with respect to the X-ray energies in increments of 0.5 keV. The square marks in FIG. 3 represent the mass attenuation coefficients of the second substance (e.g., water) with respect to the X-ray energies in increments of 0.5 keV.

Reference symbol As in FIG. 3 denotes the first attenuation coefficient ratio. More specifically, "As" represents the ratio (0.363/0.246=1.475) of the mass attenuation coefficient (0.363) of the first energy (49 keV) to the mass attenuation coefficient (0.246) of the second energy (66 key) with respect to the first substance. Reference symbol Bs in FIG. 3 denotes the second attenuation coefficient ratio. More specifically, "Bs" represents the ratio (0.233/0.197=1.187) of the mass attenuation coefficient (0.233) of the first energy (49 keV) to the mass attenuation coefficient (0.197) of the second energy (66 keV) with respect to the second substance.

The attenuation coefficient storage unit 197 may store the mass attenuation coefficient dependence of each of the first and second substances on X-ray energy. FIG. 4 is a graph showing the mass attenuation coefficient dependence of each of the first and second substances on X-ray energy. The abscissa in FIG. 4 represents X-ray energies in keV. The ordinate in FIG. 4 represents mass attenuation coefficients. The triangle marks in FIG. 4 represent the mass attenuation coefficient dependence of the first substance (e.g., the bone or contrast medium) on X-ray energy in increments of 0.5 keV. The square marks in FIG. 4 represent the mass attenuation coefficient dependence of the second substance (e.g., water) on X-ray energy in increments of 0.5 keV. Note that the X-ray energies fall within the range of 49 key to 66 keV, and the mass attenuation coefficients fall within the range of 0.15 to 0.4. However, these ranges may be broader. In this case, the image processing apparatus 19 includes attenuation coefficient calculation unit (not shown). The attenuation coefficient calculation unit calculates the first and second attenuation coefficients based on the mass attenuation coefficient dependences on X-ray energies. The attenuation coefficient calculation unit calculates the normalized attenuation coefficients of the first and second substances at the target energy based on the mass attenuation coefficient dependences of the first and second substances on X-ray energies and the target energy input via the input unit 201 (to be described later).

The estimation unit 199 estimates the abundance ratio of one of the first and second substances to the other for each pixel of the first and second medical images based on a quotient in the division map, the first attenuation ratio (As), and the second attenuation ratio (Bs). More specifically, the estimation unit 199 compares the quotient with the first and second attenuation ratios. If the quotient is equal to or more than the first attenuation ratio (As) (quotient≥As), the estimation unit 199 estimates that the abundance ratios of the first and second substances in the pixel (to be referred to as the quotient-associated pixel hereinafter) of the first and second medical images which is associated with the calculation of the quotient are 100% and 0%, respectively. If the quotient is equal to or less than the second attenuation ratio (Bs) (Bs ≥quotient), the estimation unit 199 estimates that the abundance ratios of the first and second substances in the quotient-associated pixel are 0% and 100%, respectively.

If the quotient is less than the first attenuation ratio (As) and larger than the second attenuation ratio (Bs) (Bs<quotient<As), the estimation unit 199 estimates the abundance ratios of the first and second substances in a quotient-associated pixel by the following processing. First of all, the estimation unit 199 calculates a value (As−Bs) by subtracting the second attenuation ratio (Bs) from the first attenuation ratio (As). Note that the attenuation coefficient storage unit 197 may store As−Bs in advance. The estimation unit 199 calculates a value (quotient−Bs) by subtracting the second attenuation coefficient ratio (Bs) from the quotient for each pixel in the division map. The estimation unit 199 calculates a ratio (to be referred to as the first ratio hereinafter) of (quotient−Bs) to (As−Bs). The estimation unit 199 applies the calculated first ratio to the abundance ratio of the first substance in the quotient-associated pixel. The estimation unit 199 applies a value (1−first ratio) obtained by subtracting the calculated first ratio from 1 to the abundance ratio of the second substance in the quotient-associated pixel.

If the quotient is less than the first attenuation ratio (As) and larger than second attenuation ratio (Bs) (Bs<quotient<As), the estimation unit 199 may estimate the abundance ratios of the first and second substances in the quotient-associated pixel by the following processing. The estimation unit 199 calculates a value (Bs−As) by subtracting the first attenuation ratio (As) from the second attenuation ratio (Bs). Note that the attenuation coefficient storage unit 197 may store Bs−As in advance. The estimation unit 199 calculates a value (quotient−As) by subtracting the first attenuation ratio (As) from the quotient for each pixel in the division map. The estimation unit 199 calculates a ratio (to be referred to as the second ratio hereinafter) of (quotient−As) to (Bs−As). The estimation unit 199 applies the calculated second ratio to the abundance ratio of the second substance in the quotient-associated pixel. The estimation unit 199 applies a value (1−second ratio) obtained by subtracting the calculated second ratio from 1 to the abundance ratio of the first substance in the quotient-associated pixel.

The input unit 201 inputs the imaging conditions for X-ray computed tomography, image processing conditions, and the like desired by the operator. The imaging conditions include, for example, the settings of a plurality of tube voltages or a plurality of X-ray energies. The image processing conditions include selection of energies (first and second energies) associated with medical images to be combined and settings of target energies. The input unit 201 inputs various kinds of instructions, commands, information, selections, and settings from the operator to the image processing apparatus 19. The input various kinds of instructions, commands, information, selections, and settings are output to the image processing control unit 207, the control unit 17, and the combination ratio determination unit 203 (which will be described later). The input unit 201 includes a trackball, switch buttons, a mouse, and a keyboard (none of which are shown) which are used for setting a region of interest (to be referred to as an ROI hereinafter) and the like. The input unit 201 detects the coordinates of the cursor displayed on the display screen, and outputs the detected coordinates to the control unit 17. Note that the input unit 201 may be a touch panel provided so as to cover the display screen. In this case, the input unit 201 detects touched and indicated coordinates by a coordinate reading principle such as an electromagnetic induction system, a magnetostriction system, a pressure-sensitive system, or the like, and outputs the detected coordinates to the control unit 17.

The combination ratio determination unit 203 determines the combination ratio of pixel values between the first and second medical images for each pixel based on the normalized attenuation coefficient of the first substance associated with the target energy and the normalized attenuation coefficient of the second substance associated with the target energy.

More specifically, if the abundance ratio of the first substance in a quotient-associated pixel is 100%, the combination ratio determination unit 203 reads out the normalized attenuation coefficient of the first substance corresponding to the target energy input via the input unit 201 from the attenuation coefficient storage unit 197. The combination ratio determination unit 203 determines a combination ratio corresponding to the pixel value of the quotient-associated pixel of each of the first and second medical images based on the readout normalized attenuation coefficient of the first substance. If, for example, the target energy input via the input unit 201 is 57 keV, the combination ratio determination unit 203 determines the normalized attenuation coefficient of 57 keV associated with the first substance as the first combination ratio to multiply the pixel value of the quotient-associated pixel in the first medical image. The combination ratio determination unit 203 determines the value obtained by subtracting the normalized attenuation coefficient of 57 keV associated with the first substance from 1 as the second combination ratio to multiply the pixel value of the quotient-associated pixel in the second medical image.

If the abundance ratio of the second substance in the quotient-associated pixel is 100%, the combination ratio determination unit 203 reads out the normalized attenuation coefficient of the second substance corresponding to the target energy input via the input unit 201 from the attenuation coefficient storage unit 197. The combination ratio determination unit 203 determines a combination ratio corresponding to the pixel value of the quotient-associated pixel of each of the first and second medical images based on the readout normalized attenuation coefficient of the second substance. If, for example, the target energy input via the input unit 201 is 57 keV, the combination ratio determination unit 203 determines the normalized attenuation coefficient of 57 keV associated with the second substance as the first combination ratio to multiply the pixel value of the quotient-associated pixel in the first medical image. The combination ratio determination unit 203 determines the value obtained by subtracting the normalized attenuation coefficient of 57 keV associated with the second substance from 1 as the second combination ratio to multiply the pixel value of the quotient-associated pixel in the second medical image.

If the abundance ratios of the first and second substances estimated by the estimation unit 199 are both less than 100, the combination ratio determination unit 203 determines the first and second combination ratios by linearly interpolating the normalized attenuation coefficients of the first and second substances corresponding to the target energy input via the input unit 201 with the abundance ratios of the first and second substances. More specifically, the combination ratio determination unit 203 reads out the normalized attenuation coefficients of the first and second substances corresponding to the target energy input via the input unit 201 from the attenuation coefficient storage unit 197. The combination ratio determination unit 203 determines the first combination ratio to multiply the pixel value of the quotient-associated pixel in the first medical image by multiplying the readout normalized attenuation coefficient of the first substance by the abundance ratio of the first substance. The combination ratio determination unit 203 determines the second combination ratio to multiply the pixel value of the quotient-associated pixel in the second medical image by multiplying the readout normalized attenuation coefficient of the second substance by the abundance ratio of the second substance.

Figure 5:
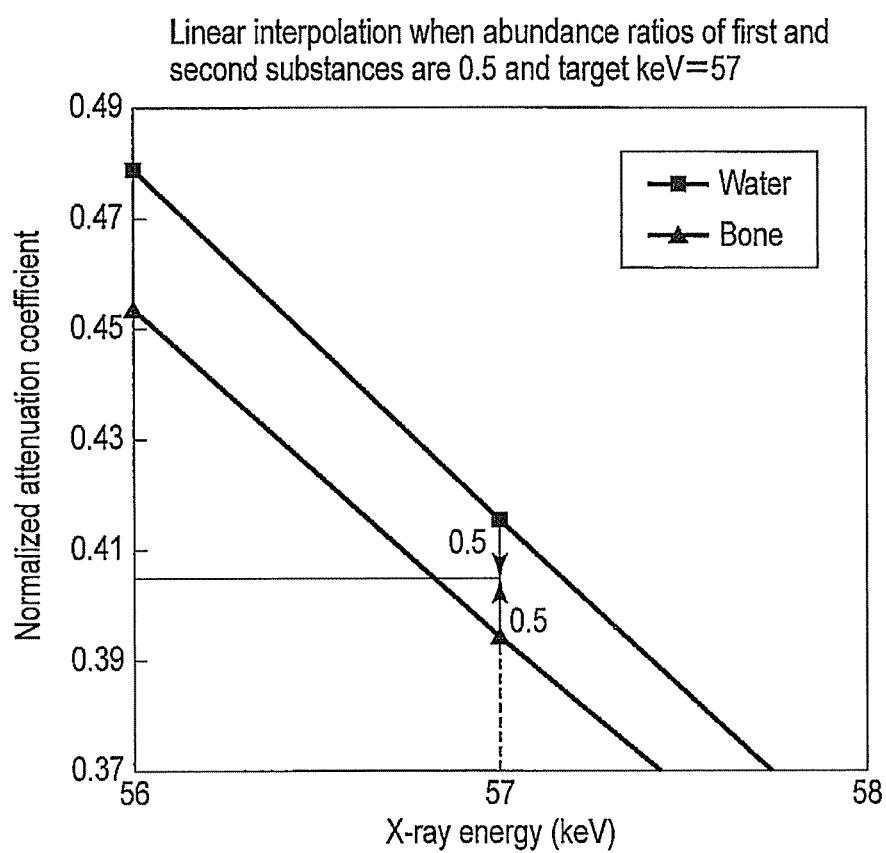
FIG. 5 is a graph showing linear interpolation by the abundance ratio of each of the first and second substances, together with the normalized attenuation coefficient dependence of each of the first and second substances on target energy, according to the first embodiment.

FIG. 5 is a graph showing the linear interpolation using the abundance ratios of the first and second substances, together with the normalized attenuation coefficients of the first and second substances corresponding to the target energy. Referring to FIG. 5, the target energy is 57 keV, and the abundance ratios of the first and second substances are both 0.5. Referring to FIG. 5, the triangle mark and the straight line passing through the triangle mark represent the normalized attenuation coefficient dependence of the first substance (bone) on X-ray energy. Referring to FIG. 5, the square mark and the straight line passing through the square mark represent the normalized attenuation coefficient dependence of the second substance (water) on X-ray energy. The first and second combination ratios are determined by executing linear interpolation using the abundance ratios of the first and second substances for the widths of normalized attenuation coefficients at the target energy on these two straight lines.

The combined image generation unit 205 generates a combined image associated with the target energy from the first and second medical images by using the first and second combination ratios determined by the combination ratio determination unit 203. More specifically, the combined image generation unit 205 adds the value obtained by multiplying the pixel value of the first medical image by the first combination ratio to the value obtained by multiplying the pixel value of the second medical image by the second combination ratio. The combined image generation unit 205 generates a combined image associated with the target energy by executing the above addition for each pixel. The display unit 15 displays the generated combined image together with the target energy. Note that the first and second combination ratios respectively correspond to weights to multiply the pixel values of a plurality of pixels in the quotient-associated pixel.

The image processing control unit 207 functions as the main unit of the image processing apparatus 19. The image processing control unit 207 includes a CPU and memory (not shown). The image processing control unit 207 controls the respective units of the image processing apparatus 19 in accordance with control programs for image processing stored in a memory (not shown). More specifically, the image processing control unit 207 temporarily stores, in a memory (not shown), information such as operator's instructions, image processing conditions, and X-ray energies associated with medical images sent from the input unit 201 and a radiology information management system (not shown), a hospital information system (not shown), and the like. The image processing control unit 207 controls the respective units of the image processing apparatus 19 based on these pieces of information temporarily stored in the memory. The image processing control unit 207 expands control programs for executing predetermined image generating and displaying operations and the like in its own memory, and executes computation, processing, and the like associated with various kinds of processes.

The image processing control unit 207 calculates an index for evaluating the low-contrast resolution of the combined image generated by the combined image generation unit 205. More specifically, an index for evaluating low-contrast resolution is, for example, a contrast noise ratio (to be referred to as a CNR hereinafter). A CNR is an index associated with the contrast between the ROI set in a combined image and the background of the combined image. It is possible to display the calculated CNR on the display unit 15, together with, for example, the combined image. Note that the image storage unit 191 can store the CNR together with the combined image. This clarifies the degree of improvement in contrast and the degree of reduction in noise. Note that the image processing control unit 207 may calculate another index such as a DEI (Dose Efficiency Index) instead of a CNR.

Before calculation of a CNR, an ROI is set in the combined image via the input unit 201. The image processing control unit 207 calculates the average value (to be referred to as an ROI average value hereinafter) of the Hounsfield Units (to be refereed to as HUs hereinafter) in the ROI in the combined image. The image processing control unit 207 calculates the average value of HUs of the overall combined image (to be referred to as an overall average value hereinafter). The image processing control unit 207 calculates the standard deviation (to be referred to as an overall standard deviation hereinafter) of HUs in the overall combined image. The image processing control unit 207 calculates a CNR by using the ROI average value, overall average value, and overall standard deviation. More specifically, the image processing control unit 207 divides the difference value obtained by subtracting the overall average value from the ROI average value by the overall standard deviation. Note that the image processing control unit 207 may calculate an ROI average value, overall average value, and overall standard deviation by using the pixel values of the combined image. The image processing control unit 207 can also calculate the overall average value of the area of the combined image from which the ROI is excluded. In addition, the image processing control unit 207 may calculate, as a CNR, the square root of the quotient obtained by dividing the difference value obtained by subtracting the square of the overall average from the square of the ROI average value by the square of the overall standard deviation.

(Monochrome X-ray Image Generation Function)

The monochrome X-ray image generation function is a function of generating a medical image associated with a target energy from the first and second medical images in accordance with the abundance ratios of the first and second substances and the normalized attenuation coefficient of the target energy. Processing according to the monochrome X-ray image generation function (to be referred to as monochrome X-ray image generation processing hereinafter) will be described below.

Figure 6:
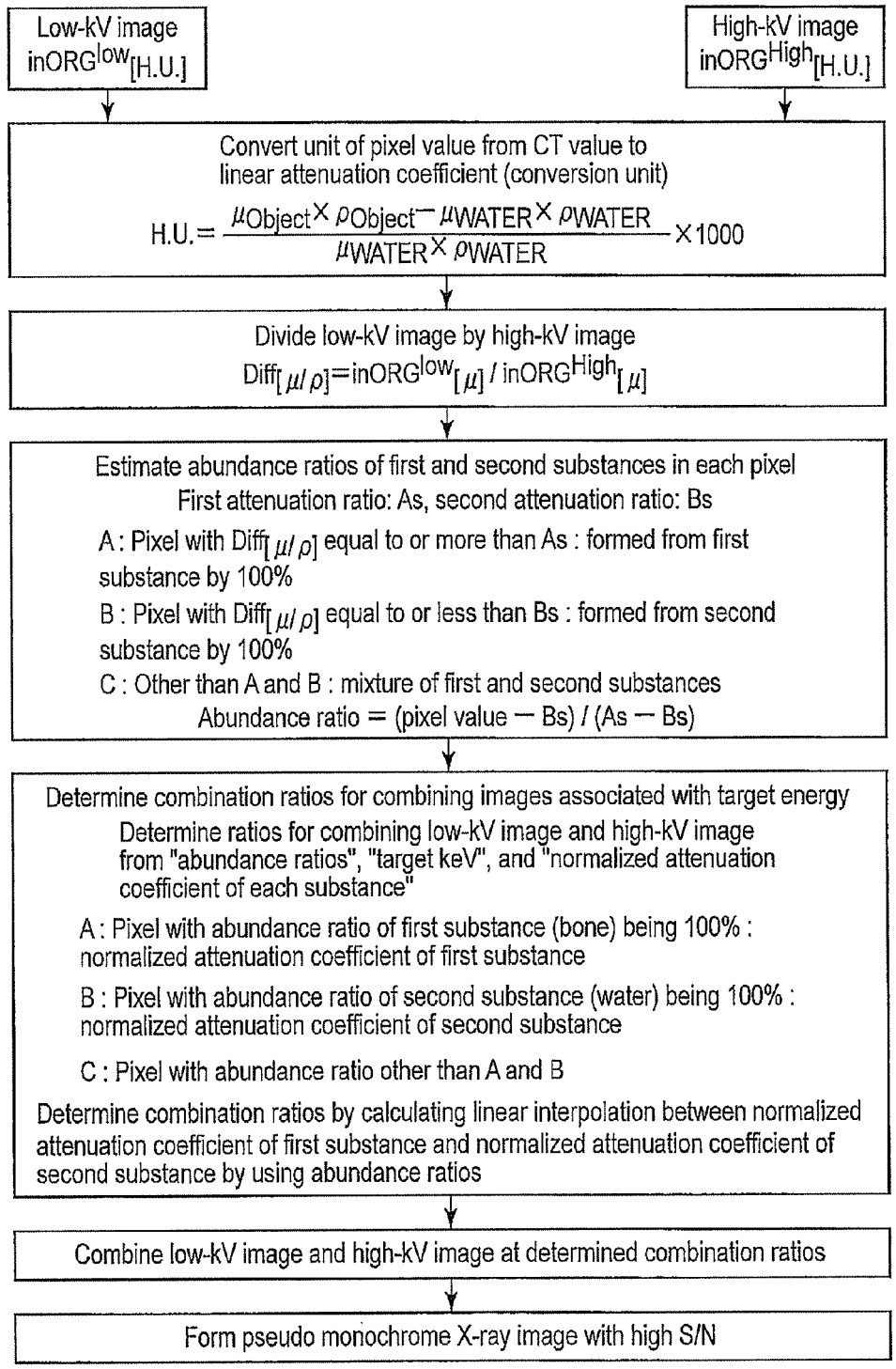
FIG. 6 is a schematic view showing an outline of a procedure for combining two medical images originating from X-rays of two different kinds of energies according to the first embodiment.

FIG. 6 is a schematic view showing an outline of monochrome X-ray image generation processing. The conversion unit 193 receives an image with a low tube voltage (low-kV image) and an image with a high tube voltage (high-kV image). The unit of pixel values is converted from a CT value to a linear attenuation coefficient for each pixel. Reference symbol $\mu$ denotes a mass attenuation coefficient; and $\rho$, a density. This conversion corresponds to solving $\mu\_Object \cdot \rho\_Object$. After conversion to a linear attenuation coefficient, the pixel value (linear attenuation coefficient) of a low-kV image is divided by the pixel value (linear attenuation coefficient) of a high-kV image. At this time, $\rho\_Object$ is canceled down, and hence the unit of the value (Diff) obtained by division is the unit of mass attenuation coefficient. The value obtained by division is compared with the first attenuation ratio (As) and the second attenuation ratio (Bs). This comparison will estimate the abundance ratios of the first substance (contrast medium or bone) and second substance (water). Combination ratios respectively corresponding to the pixel values of the low-kV image and high-kV image are determined based on the abundance ratios and the normalized attenuation coefficients of the first and second substances associated with the target energy (keV). The low-kV image is combined with the high kV-image in accordance with the determined combination ratios. This will obtain an image corresponding to the target energy (monochrome) with a high S/N (Signal/Noise ratio).

Figure 7:
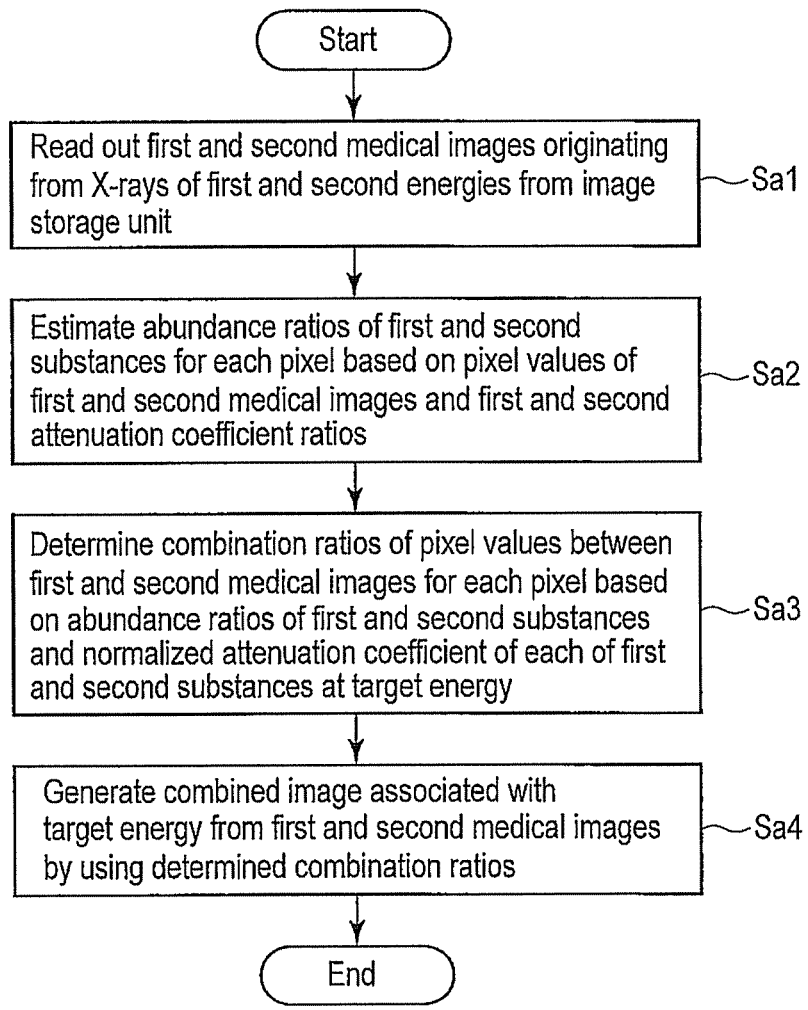
FIG. 7 is a flowchart showing a procedure in the schematic view of FIG. 6 according to the first embodiment.

FIG. 7 is a flowchart showing a procedure for monochrome X-ray image generation processing. The apparatus reads out the first and second medical images originating from X-rays of the first and second energies from the image storage unit 191 (step Sa1). If the image storage unit 191 stores a plurality of medical images respectively originated from a plurality of X-ray energies, the apparatus selects two different kinds of X-ray energies before the processing in step Sa1 in accordance with the instruction input from the operator via the input unit 201.

The apparatus estimates the abundance ratios of the first and second substances for each pixel based on the pixel values of the readout first and second medical images, the first attenuation ratio (As), and the second attenuation ratio (Bs) (step Sa2). The reason why the apparatus estimates the abundance ratios of the first and second substances will be described in detail in association with the abundance ratio estimation function to be described below. The apparatus determines the combination ratios of pixel values between the first and second medical images for each pixel based on the abundance ratios of the first and second substances and the normalized attenuation coefficients of the first and second substances at the target energy (step Sa3). The processing of determining the combination ratios of pixel values between the first and second medical images will be described in detail in association with the combination ratio determination function to be described below. The apparatus generates a combined image associated with the target energy from the first and second medical images in accordance with the determined combination ratios (step Sa4).

(Abundance Ratio Estimation Function)

The abundance ratio estimation function is a function of estimating the abundance ratios of the first and second substances for each pixel based on the pixel values of the first and second medical images and the first and second attenuation coefficient ratios. The processing according to the abundance ratio estimation function (to be referred to as abundance ratio estimation processing hereinafter) will be described below.

Figure 8:
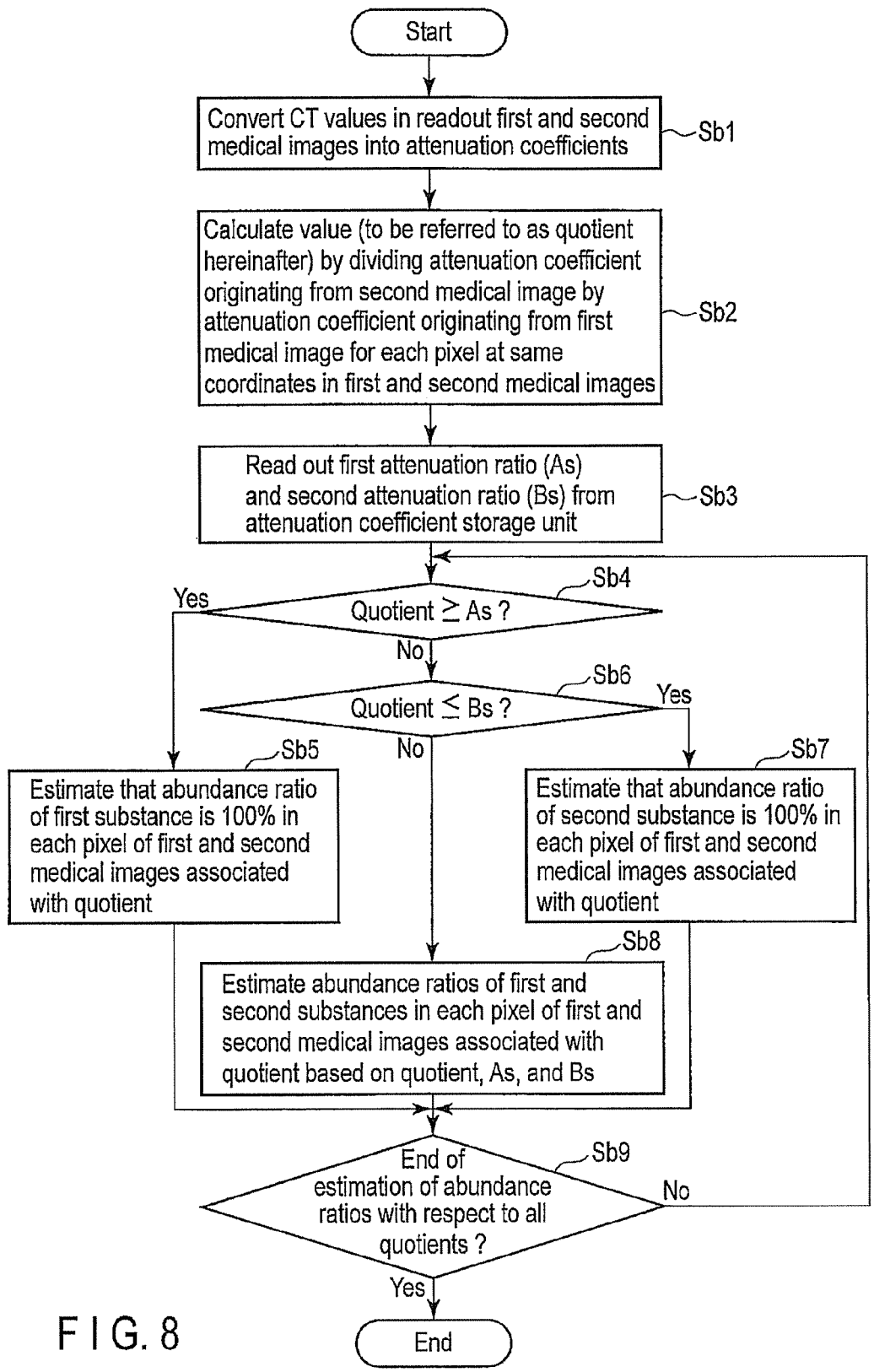
FIG. 8 is a flowchart showing a procedure for processing in step Sa2 in FIG. 7 according to the first embodiment.

FIG. 8 is a flowchart showing a procedure for abundance ratio estimation processing in step Sa2 in FIG. 7.

The apparatus converts CT values in the readout first and second medical images into attenuation coefficients (step Sb1). The apparatus calculates a value (quotient) by dividing an attenuation coefficient originating from the second medical image by an attenuation coefficient originating from the first medical image for each pixel at the same coordinates in the first and second medical images (step Sb2). The apparatus reads out the first attenuation ratio (As) and the second attenuation ratio (Bs) from the attenuation coefficient storage unit 197 (step Sb3).

The apparatus compares the quotient with the first attenuation ratio (As) (step Sb4). If the quotient is equal to or more than As, the apparatus estimates that the abundance ratio of the first substance in each of the pixels of the first and second medical images which are associated with the quotient is 100% (step Sb5). At this time, the abundance ratio of the second material is estimated to 0%. If the quotient is less than As, the apparatus compares the quotient with the second attenuation coefficient (Bs) (step Sb6). If the quotient is equal to or less than Bs, the apparatus estimates that the abundance ratio of the second substance in each of the pixels of the first and second medical images which are associated with the quotient is 100%. At this time, the abundance ratio of the first substance is estimated to 0% (step Sb7).

If the quotient is larger than Bs (Bs<quotient<As), the apparatus estimates the abundance ratios of the first and second substances in each of pixels of the first and second medical images based on the quotient, the first attenuation coefficient ratio (As), and the second attenuation coefficient ratio (Bs) (step Sb8). The apparatus repeats the processing in step Sb4 to the processing in step Sb8 until the apparatus estimates the abundance ratios of the first and second substances for all the quotients calculated in the processing in step Sb2 (step Sb9).

(Combination Ratio Determination Function)

The combination ratio determination function is a function of determining the combination ratios of pixel values between the first and second medical images based on the abundance ratios of the first and second substances and the normalized attenuation coefficients of the first and second substances associated with the target energy. The processing according to the combination ratio determination function (to be referred to as combination ratio determination processing hereinafter) will be described below.

FIG. 9 is a flowchart showing a procedure for combination ratio determination processing in step Sa3 in FIG. 7.

The operator inputs a target X-ray energy (target energy) via the input unit 201 (step Sc1). The apparatus determines whether the abundance ratio of the first substance in pixels of the first and second medical images is 100% (step Sc2). If the abundance ratio of the first substance is 100%, the apparatus determines combination ratios respectively corresponding to the pixel values of the first and second medical images based on the normalized attenuation coefficient of the first substance associated with the target energy (step Sc3). If the abundance ratio of the first substance is not 100%, the apparatus determines whether the abundance ratio of the second substance in the pixels of the first and second medical images is 100% (step Sc4). If the abundance ratio of the second substance is 100%, the apparatus determines combination ratios respectively corresponding to the pixel values of the first and second medical images based on the normalized attenuation coefficient of the second substance associated with the target energy (step Sc5).

If neither of the abundance ratios of the first and second substances is 100%, the apparatus determines combination ratios respectively corresponding to the pixel values of the first and second medical images based on the normalized attenuation coefficients of the first and second substances corresponding to the target energy and the abundance ratios of the first and second substances (step Sc6).

Figure 10:
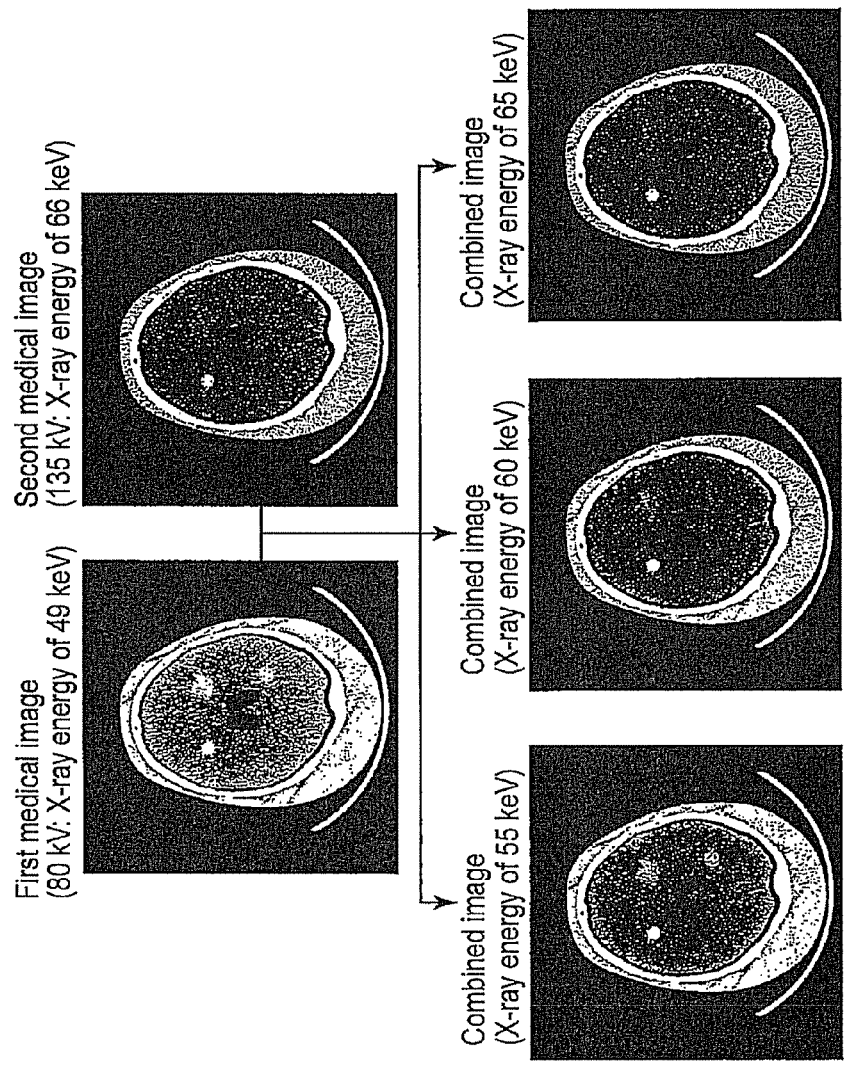
FIG. 10 is a view showing examples of combined images generated by a combined image generation unit, together with a plurality of target energies, according to the first embodiment.

FIG. 10 is a view showing examples of combined images output from the combined image generation unit 205, together with a plurality of target energies. The tube voltage associated with the first medical image is 80 kV (the first energy is 49 keV). The tube voltage associated with the second medical image is 135 kV (the first energy is 66 keV). Based on these medical images, the apparatus outputs a plurality of medical images respectively corresponding to a plurality of target energies (55 keV, 60 keV, and 65 keV).

he above arrangement can obtain the following effects.

The X-ray computed tomography apparatus 1 according to this embodiment can generate a medical image corresponding to the X-ray energy desired by the operator in a short period of time with high contrast and low noise by using two kinds of medical images respectively corresponding to two different kinds of X-ray energies. More specifically, the X-ray computed tomography apparatus 1 according to this embodiment can estimate the abundance ratios of the first and second substances for each pixel based on the pixel values of a two kinds of medical images respectively corresponding to two different kinds of X-ray energies, the attenuation coefficient of the first substance, and the attenuation coefficient of the second substance. The apparatus can determine the combination ratios of pixel values between the first and second medical images for each pixel based on the estimated abundance ratios of the first and second substances and the normalized attenuation coefficient of each of the first and second substances which is associated with the target energy. The apparatus can generate a combined image associated with the target energy from the first and second medical images based on the determined combination ratios. This makes it possible to generate a medical image corresponding to the X-ray energy desired by the operator (target energy) by using medical images respectively corresponding to the two different types of X-ray energies in a short period of time with high contrast and low noise. In addition, the X-ray computed tomography apparatus 1 can calculate an index for evaluation low-contrast resolution, such as a CNR, for a generated combined image. This can evaluate low-contrast resolution. In addition, it is possible to display or store an improvement in the contrast of a combined image and the degree of reduction in noise.

Note that when the technical idea of the X-ray computed tomography apparatus 1 is to be implemented by a medical image processing apparatus as a modification of this embodiment, the apparatus includes, for example, the constituent elements within the dotted line (image processing apparatus 19) in the block diagram of FIG. 1. Each process in the monochrome X-ray image generation function, abundance ratio estimation function, and combination ratio determination function is the same as that in the first embodiment. In addition, each function associated with each embodiment can also be implemented by installing programs for executing the corresponding processing in a computer such as a workstation and expanding them in a memory. In this case, the programs which can cause the computer to execute the corresponding techniques can be distributed by being stored in recording media such as magnetic disks ((floppy®) disks, hard disks, and the like), optical disks (CD-ROMs, DVDs, and the like), and semiconductor memories.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
an image storage unit configured to store a first medical image and a second medical image having pixels respectively originating from X-rays of a first energy and a second energy;
a conversion unit connected to said image storage unit for converting a pixel value of the first medical image and the second medical image into a mass attenuation coefficient for each of the pixels to generate a first attenuation map and a second attenuation map;
a quotient calculation unit connected to said conversion unit for generating a quotient based upon the first attenuation map and the second attenuation map and storing the quotient in a division map;

an estimation unit connected to said quotient calculation unit for estimating an abundance ratio of one of a first substance and a second substance to the other for each of the pixels based on the quotient in the division map, a first attenuation coefficient ratio of the first substance which correspond to the first energy and the second energy, and a second attenuation coefficient ratio of the second substance which correspond to the first energy and the second energy, said estimation unit comparing the quotient with at least one of the first attenuation coefficient ratio (As) and the second attenuation ratio (Bs) to estimate the abundance ratio;

a combination ratio determination unit configured to determine combination ratios of pixel values between the first medical image and the second medical image for each of the pixels based on the abundance ratios of the first substance and the second substance and normalized attenuation coefficients of the first substance and the second substance which are associated with a target energy; and a combined image generation unit configured to generate a combined image associated with the target energy from the first medical image and the second medical image by using the determined combination ratios.

2. An X-ray computed tomography apparatus comprising:

an X-ray generation unit configured to generate X-rays;

an X-ray detection unit configured to detect X-rays generated from the X-ray generation unit and transmitted through an object;

a reconstruction unit configured to reconstruct a first medical image and a second medical image having pixels respectively originating from X-rays of a first energy and X-rays of a second energy based on outputs from the X-ray detection unit;

a conversion unit for converting a pixel value of the first medical image and the second medical image into a mass attenuation coefficient for each of the pixels to generate a first attenuation map and a second attenuation map;

a quotient calculation unit connected to said conversion unit for generating a quotient based upon the first attenuation map and the second attenuation map and storing the quotient in a division map;

an estimation unit connected to said quotient calculation unit for estimating an abundance ratio of one of a first substance and a second substance to the other for each of the pixels based on the quotient in the division map, a first attenuation coefficient ratio of the first substance which correspond to the first energy and the second energy, and a second attenuation coefficient ratio of the second substance which correspond to the first energy and the second energy, said estimation unit comparing the quotient with at least one of the first attenuation coefficient ratio (As) and the second attenuation coefficient ratio (Bs) to estimate the abundance ratio;

a combination ratio determination unit configured to determine combination ratios of pixel values between the first medical image and the second medical image for each of the pixels based on the abundance ratios of the first substance and the second substance and normalized attenuation coefficients of the first substance and the second substance which are associated with a target energy; and a combined image generation unit configured to generate a combined image associated with the target energy from the first medical image and the second medical image by using the determined combination ratios.

* * * * *